(12) United States Patent
Blank

(10) Patent No.: US 12,090,296 B2
(45) Date of Patent: Sep. 17, 2024

(54) LINEAR DRIVE FOR PIGMENTATION DEVICES

(71) Applicant: LONG-TIME-LINER CONTURE MAKE-UP GMBH, Munich (DE)

(72) Inventor: Anton Blank, Stuttgart (DE)

(73) Assignee: LONG-TIME-LINER CONTURE MAKE-UP GMBH, Munich (DE)

( * ) Notice: Subject to any disclaimer, the term of this patent is extended or adjusted under 35 U.S.C. 154(b) by 512 days.

(21) Appl. No.: 17/422,253

(22) PCT Filed: Jan. 10, 2020

(86) PCT No.: PCT/EP2020/050583
§ 371 (c)(1),
(2) Date: Jul. 12, 2021

(87) PCT Pub. No.: WO2020/144352
PCT Pub. Date: Jul. 16, 2020

(65) Prior Publication Data
US 2022/0040467 A1     Feb. 10, 2022

(30) Foreign Application Priority Data

Jan. 13, 2019 (DE) .......................... 102019000135.4

(51) Int. Cl.
| | |
|---|---|
| *H02K 1/16* | (2006.01) |
| *A61M 37/00* | (2006.01) |
| *H02K 41/02* | (2006.01) |
| *H02P 25/06* | (2016.01) |

(52) U.S. Cl.
CPC ........... *A61M 37/0076* (2013.01); *H02K 1/16* (2013.01); *H02K 41/02* (2013.01); *H02P 25/06* (2013.01); *A61M 2205/106* (2013.01)

(58) Field of Classification Search
CPC ........ H02K 1/16; H02K 41/02; H01F 7/1646; H02P 25/032; H02P 25/06; H02P 8/10; H02P 8/02; A61M 37/0076
See application file for complete search history.

(56) References Cited

U.S. PATENT DOCUMENTS

| | | | |
|---|---|---|---|
| 5,436,518 A * | 7/1995 | Kawai | .................... H02K 41/06 318/135 |
| 2017/0207690 A1 | 7/2017 | Paweletz et al. | |
| 2017/0293272 A1 | 10/2017 | Jeong et al. | |

FOREIGN PATENT DOCUMENTS

| | | |
|---|---|---|
| CN | 108884814 A | 11/2018 |
| DE | 19509195 A1 | 9/1996 |
| DE | 102016008129 A1 | 1/2018 |
| EP | 0967316 A2 | 12/1999 |

(Continued)

OTHER PUBLICATIONS

International Search Report of PCT/EP2020/050583 dated Apr. 7, 2020 [PCT/ISA/210].

*Primary Examiner* — Leda T Pham
(74) *Attorney, Agent, or Firm* — Sughrue Mion, PLLC

(57) ABSTRACT

A linear drive for pigmentation devices, comprising a stator, an air gap which is provided in the stator and is formed so as to be offset in a defined manner, an electric coil within the stator, said coil being designed to produce a concentration of the magnetic flux in the air gap as a result of the coil being energized, an armature which is designed to carry out sliding axial movements in the stator, and a permanent magnet which is captively connected to the armature.

5 Claims, 1 Drawing Sheet

(56) References Cited

FOREIGN PATENT DOCUMENTS

Figure 1:
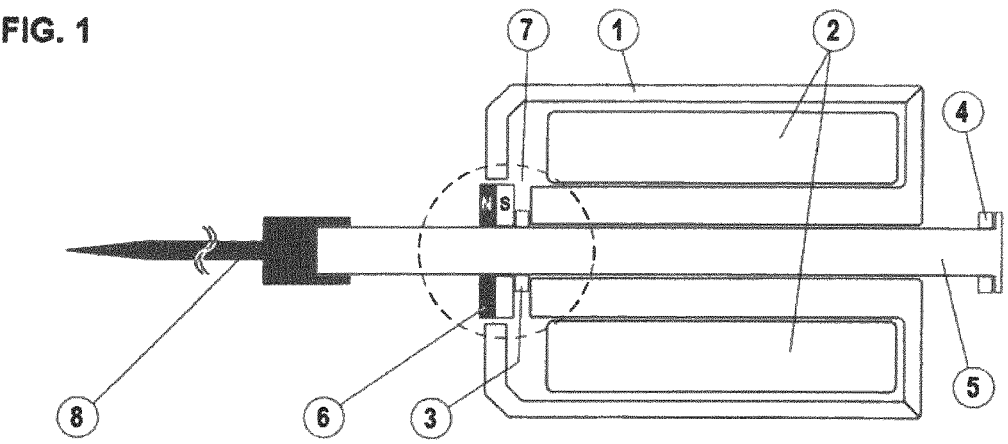

| KR | 10-2018-0066514 A | 6/2018 |
|---|---|---|
| TW | 201443942 A | 11/2014 |

* cited by examiner

LINEAR DRIVE FOR PIGMENTATION DEVICES

CROSS REFERENCE TO RELATED APPLICATIONS

This application is a National Stage of International Application No. PCT/EP2020/050583, filed Jan. 10, 2020, claiming priority to German Patent Application No. 10 2019 000 135.4, filed Jan. 13, 2019.

The invention relates to a linear drive for pigmentation devices.

BACKGROUND AND PRIOR ART

Pigmentation devices are tattooing devices designed specifically for the needs of application of permanent make-up, also referred to as Permanent Make-Up (PMU). Said devices are designed as hand-held devices for inserting fine tattoos by pricking mainly into the skin of the face. For the application of PMU, pointed pricking means, preferably needles, are used to insert liquid color materials by pricking, mainly in line form into the skin of the face, where said liquid color materials are then to remain for a longer period of time.

For the PMU, as well as for the tattooing, the color materials must be inserted through the epidermis (uppermost skin layer) into the upper layer of the live living dermis, so that a longer durability can be achieved, since the epidermis is constantly renewed by the organism within approximately 4 weeks. From the thickness of the epidermis of 0.05-0.2 mm and an insertion depth of the color materials into the living dermis of 0.05 mm to 0.1 mm results the total pricking depth into the skin, which thus amounts to approximately 0.1 mm-0.3 mm.

The liquid color materials are inserted by a reciprocating pricking means, the tip of which wets itself in the respective retracted position from a color reservoir and which inserts the color material into the skin during deployment. The pricking depth into the skin must be determined by the user, who by observing the needle tip and the skin identifies whether they reach the living dermis.

For inserting the color materials, a reciprocating needle movement is required, which must travel strictly axially without radial components. For driving the pricking means, pigmentation devices mainly use rotating motors whose rotary motion is converted into axial reciprocating motion by a variety of different transmission types. On the market there are also linear motors based on the electromagnetic plunger principle, which do not require a gearbox.

All drives for pigmentation devices available on the market have in common that their resulting reciprocating motion has a periodic, almost harmonic sinusoidal curve shape based on the physical oscillation laws and whose maximum motion speed required for pigmentation is directly dependent on the drive stroke and its repetition frequency.

The stroke of the drives in the prior art remains at about 2 mm despite the small pricking depths required. The reason for the rather large stroke in comparison to the small pricking depths is that for each pricking movement a renewed wetting of the tip of the pricking means in a color reservoir is required, which can only be reached in the retracted position of the pricking means and the color reservoir must not be too close to the tip of the device so that the user can still work with sufficient distance of the color reservoir to the skin.

The skin is an elastic tissue. When the pricking means hits the skin, the skin first dents according to its penetration resistance and elasticity, depending on the prick-in velocity, and is then punctured by the needle tip at an individual energy level for each skin property and skin region. The drive must present suitable properties with regard to the range of individually occurring skin properties in order to insert the color materials into the predetermined depth of the resilient skin. The important properties of the drive are its inherent vibrations, which are transmitted directly to the needle, its repeatable prick-in velocity and the repetition frequency of the pricking movement. Low axial natural vibrations allow the user to manually approach and maintain the pricking depth of 0.1-0.3 mm during pigmentation, low radial natural vibrations ensure lines devoid of lateral tipping. High prick-in velocity facilitates low indentations of the skin and thus a pricking depth that is easier to be kept at a constant level manually, which improves the quality of the pigmentation. Low repetition frequency protects the skin by setting only as many stitches in a row as required for visually closed lines in relation to the travel speed.

The known drives/hand-held devices have a total mass of 80 g on average and operate in a frequency band of 50-200 Hz, although in practice there is usually chosen a frequency of around 100 Hz. At 100 Hz, a stroke of 2 mm and the unavoidable moving masses of the transmission or plunger armature, there arise considerable acceleration forces which result in undesirable axial and/or radial vibrations of the light hand-held device. Measurements have shown that the vibration amplitudes of the known PMU devices exceed on average 0.5 mm. With pricking depths of only 0.1-0.3 mm, such vibration amplitudes are detrimental to precise working in depth and/or with regard to lateral consistency for pigmentation quality and skin protection. Besides, the axial vibrations have an adverse effect on the prick-in velocity and reduce it considerably.

The known drives/hand-held devices do not provide sufficient properties with regard to the prick-in velocity. The periodic, almost harmonic, sinusoidal path-time curves show only minimal prick-in velocity at a pricking depth of 0.1-0.3 mm, since the pricking means is already shortly before the reversal point of the sinusoidal oscillation and is largely slowed down. Due to the penetration resistance, the too low prick-in velocity leads to large indentations of the skin by the time it can be punctured. Therefore, the user has to guide the pricking means deeper than the puncture is supposed to be by holding it forward, so that the skin fluttering in its individual natural frequency is partially punctured too deeply or too shallowly, depending on the vertical plane in which the skin that is not fluttering synchronously to the puncture frequency is located at the next puncture. Uniform color penetration in depth, uniform color intensity along the pigmented line, as well as skin-friendly and painless pigmentation are only partially possible due to the asynchrony between skin frequency and pricking frequency.

For small skin indentations, the fastest possible prick-in velocity is required, which in the prior art is only possible by setting high frequencies. Nevertheless, high frequency remains contradictory to the increasing vibrations. High frequencies additionally remain contradictory to the need of lowering the pricking frequency for skin-friendly pigmentation. Already at 50 Hz of pricking frequency and the usual travel speeds, furrow-shaped skin wounds are produced due to the strong overlapping of individual punctures. This leaves the user with a rather compromised practical application of a pricking frequency of about 100 Hz, which, however, leads to vibrations of the hand-held devices of more than 0.5 mm and is responsible for irreversible skin damage.

SUMMARY OF THE INVENTION

It is the object of the invention to create a linear drive for pigmentation devices which, in regard to the prior art, has lower vibrations and at the same time provides higher prick-in velocities at low pricking frequencies.

Pursuant to the invention, a linear drive for pigmentation devices according to the generic term of the independent claim 1 is provided, with
- a stator 1, an air gap 7 which is provided in the stator and is formed so as to be offset in a defined manner,
- an electric coil 2 within the stator 1, said coil being configured to produce a concentration of the magnetic flux 9 in the air gap 7 as a result of the coil being energized,
- an armature 5 which is configured to carry out sliding axial movements in the stator 1,
- and a permanent magnet 6 which is captively connected to the armature 5.

The linear drive for pigmentation devices is provided and configured to move the armature 5 from a non-energized stable rest position into a non-energized unstable extended position in response to the coil 2 being energized and the electromagnetic field/flux 9 concentrated in the air gap 7 mainly by means of a magnetic repulsion acting on the magnet 6, and the thickness of the stop 3 is dimensioned such that the magnetic attractive force of the permanent magnet 6 acting on the stator 1 is overcome only shortly prior to reaching the maximum electromagnetic counterforce, i.e. of the maximum operating current, by energizing the coil 2, and the energy which is then stored in the permanent magnet 6 until the release point is abruptly freed and extends the armature 5 out of the stator 1 with a high degree of acceleration.

A further development of the invention provides that the control of the extension speed of the armature 5 can be effected by means of the switch-on time of the current in the coil 2 and the switch-on time is always terminated in time during the inductive rise of the coil current.

In a preferred embodiment of the invention, it is provided that a non-harmonic periodic oscillation of the armature 5 is effected by the coil 2 always being de-energized before the extended position of the armature 5 is reached, so that the non-energized retraction movement of the armature 5 is largely constant and becomes independent of the current-controlled extension movement of the armature 5.

A further development of the invention provides that the non-energized path/time characteristic curve of the retraction movement of the armature 5, caused by the permanent magnet force/path characteristic curve of the magnetic attractive forces 10 between the magnet 6 and the stator 2, is formed by shaping the stator geometry 1 and the magnetically effective mass of said stator in such a way that the retraction time of the armature 5 is minimized in a system-related manner.

With a purposeful embodiment of the invention, it can be envisaged, that by means of the close combination of the operating frequency with the natural frequency of the linear drive, a minimization of the drive vibrations and, at the same time, a minimization of the extension time is effected.

EXEMPLARY EMBODIMENT OF THE INVENTION

Further advantages, features and details of the invention result from the following description of a preferred exemplary embodiment of the linear drive for pigmentation devices as well as from the drawings:

FIG. 1 a schematic representation of a linear drive for pigmentation devices according to the invention in rest position with non-energized coil 2.

Figure 2:
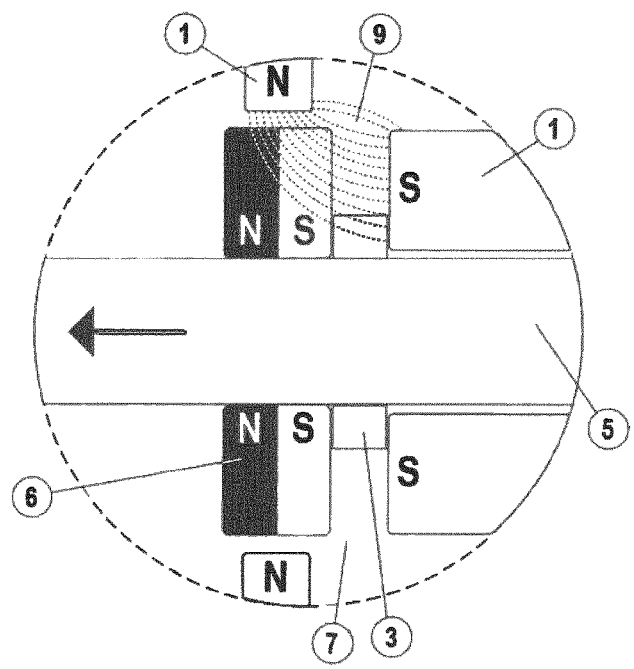

FIG. 2 an enlarged schematic representation of the air gap formed so as to be offset according to the invention of the linear drive for pigmenting devices at the moment of energizing the coil 2.

Figure 3:
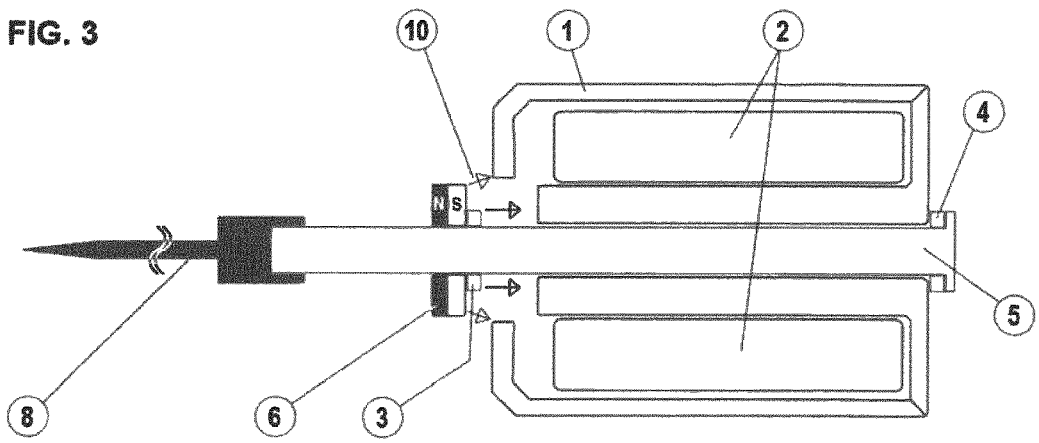

FIG. 3 a schematic representation of the linear drive for pigmentation devices according to FIG. 1, at the time of the reversal point of the extension movement with non-energized coil 2.

FIG. 1 schematically shows an example of a linear drive for pigmentation devices according to the invention in rest position without electrical control of the coil 2. The permanent magnet 6, which is captively connected to the armature 5, is in contact with the stop 3 due to its magnetic attractive forces to the ferromagnetic stator 1. The thickness of the stop 3 is so dimensioned that in the rest position the permanent magnet 6 assumes an axially central position relative to the opening of the stator 1 and that the magnetic attractive force of the permanent magnet 6 on the stator 1 is overcome by energizing the coil 2 only shortly before the maximum operating current is reached and therefore energy storage takes place in the permanent magnet 6, which is used for advantageous operation of the linear drive for pigmentation devices. The stop 4 prevents the armature 5 from falling out of the stator 1 and limits the stroke of the linear drive.

FIG. 2 shows an enlarged schematic representation of the air gap so formed as to be offset according to the invention at the time of energizing the current in the coil 2, which due to the inductance of the coil 2 increases exponentially and causes a magnetic field 9 in the air gap 7 which also increases exponentially. Due to the arrangement of the air gap 7, which is provided and formed so as to be offset in a defined manner, the electromagnetic field 9 flows through the permanent magnet 6 in a manner that is favorable for the generation of a repulsive force with a high degree of efficiency and, due to the concentration of the largest part of the magnetic energy in the air gap 7, taking into account the energy storage in the permanent magnet 6 described in [19], generates an almost abrupt repulsion of the permanent magnet 6 by the electromagnetic force 9, so that the permanent magnet 6 together with the armature 5 is extended to the stop 4 with high acceleration similar to the known snap action effect, which leads to the advantageous high prick-in velocities. The sum of the moving masses of armature 5, magnet 6 and pricking means 8 amounts to few grams, so that the armature 5 undergoes high degree of acceleration even with low forces and achieves high velocities despite the small stroke of, for example, 2 mm, and the small total mass has an advantageous effect on the vibrations of the entire system. The braking force component 10 applied to the ferromagnetic stator 1 by the attractive force of the permanent magnet 6 during extension is arranged to be degressive, so that this braking force decreases disproportionately with the distance of the magnet 6 from the stator 1, resulting in a substantially higher end speed of the armature 5 when it hits the stop 4 than is the case with the sinusoidal drives of the prior art. The variation of the speed of an extension movement is controlled via the switch-on time of the coil, which, however, contrary to the prior art, is always terminated temporally within the inductive rise of the coil current, with the advantage of being able to control the entire setting range already during the short rise. In this way, the extension speed and the pricking frequency can be advantageously predetermined for pigmentation in the factory and set by the user on the pigmentation device.

FIG. 2 shows the linear drive according to FIG. 1 at the time of the reversal point with non-energized coil 2, i.e. at the time when the armature has just changed its direction of movement to return to the rest position. The established degressive characteristic curve of the course of the permanent magnetic restoring force 10 has had an advantageous effect on a decreasing reduction of the extension speed of the armature 5 during the extension. During retraction of the armature 5, the previously degressive braking force 10 now has a progressively accelerating effect on the armature 5 and causes a return time of the armature 5 to the rest position that remains unaffected by the former extension characteristic curve, so that an advantageous non-harmonic oscillation is generated even with periodic control. For an advantageously quick backward movement of the armature 5 to its rest position, the magnetic force/path characteristic curve between the permanent magnet 6 and the stator 2 can be effected by means of its geometric shape and its ferromagnetic mass.

The features of the invention disclosed in the foregoing description, the claims and the drawings may be relevant, both individually and in any combination, to the implementation of the invention in its various embodiments.

The invention claimed is:

1. A pigmentation device with a linear drive, comprising:
a stator and an air gap which is provided in the stator and is formed so as to be offset in a defined manner;
an electric coil within the stator, the coil being configured to produce a concentration of a magnetic flux in the air gap as a result of the coil being energized,
an armature which is designed to carry out sliding axial movements in the stator, and
a permanent magnet which is fixedly connected to the armature,
wherein
the linear drive is configured to move the armature, in response to the coil being energized and an electromagnetic field concentrated in the air gap, mainly by means of magnetic repulsion acting on the permanent magnet, from a rest position in which, when the coil is de-energized, the permanent magnet holds the armature by magnetic attractive forces to the stator, into an extended position in which the armature performs a reversal of its extension movement, wherein at a time of the reversal of the extension movement the coil is de-energized and the armature reverses its extension movement in order to return to the rest position due to the magnetic attractive forces of the permanent magnet, and
a thickness of a stop, on which the permanent magnet and the stator lie in the rest position, is dimensioned in such a way that in the rest position the magnetic attractive forces of the permanent magnet acting on the stator are overcome by energizing the coil only shortly prior to reaching a maximum electromagnetic counter-force, and an energy which is then stored in the permanent magnet at this release point is abruptly freed and extends the armature out of the stator with a high degree of acceleration.

2. The pigmentation device according to claim 1, wherein a control of an extension speed of the armature, with which the armature extends from the stator, is effected by means of a switch-on duration of the coil being energized, and the switch-on duration is always terminated in time during an inductive rise of the coil current.

3. The pigmentation device according to claim 1, wherein a non-harmonic periodic oscillation of the armature is effected by the coil always being de-energized before the extended position of the armature is reached, so that a retraction movement of the armature, with which the armature returns to the rest position, is largely constant and becomes independent of the controlled extension movement of the armature via the energization of the coil.

4. The pigmentation device according to claim 1, wherein the non-energized path/time characteristic curve of a retraction movement of the armature, when the coil is de-energized, caused by the permanent magnet force/path characteristic curve of the magnetic attractive forces between the permanent magnet and the stator, is formed by shaping the stator geometry and a magnetically effective mass of said stator in such a way that the retraction time of the armature is minimized.

5. Use of the pigmentation device according to claim 1 for application of Permanent Make-Up (PMU).

* * * * *